(12) United States Patent
Guerrero et al.

(10) Patent No.: US 11,654,187 B2
(45) Date of Patent: May 23, 2023

(54) HORN FLY PROTEIN AS ACTIVE ANTIGEN IN ANTI-HORN FLY VACCINE FOR PROTECTION OF BOVINES AGAINST HORN FLY INFESTATIONS

(71) Applicant: The United States of America, as represented by the Secretary of Agriculture, Washington, DC (US)

(72) Inventors: Felicito Guerrero, Paige, TX (US); Luisa N. Domingues, College Station, TX (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 138 days.

(21) Appl. No.: 17/166,433

(22) Filed: Feb. 3, 2021

(65) Prior Publication Data

US 2022/0241387 A1   Aug. 4, 2022

(51) Int. Cl.
*A61K 39/00* (2006.01)
*A61P 43/00* (2006.01)
*A61K 39/39* (2006.01)

(52) U.S. Cl.
CPC .......... *A61K 39/0003* (2013.01); *A61K 39/39* (2013.01); *A61P 43/00* (2018.01); *A61K 2039/552* (2013.01)

(58) Field of Classification Search
None
See application file for complete search history.

(56) References Cited

PUBLICATIONS

Domingues et al. (Parasites Vectors, 14:442, 2021).*
https://rest.uniprot.org/uniprotkb/A0A1I8PBN9.txt; accessed Oct. 31, 2022).*

* cited by examiner

*Primary Examiner* — Brian Gangle
(74) *Attorney, Agent, or Firm* — John D. Fado; Mark D. McNemar

(57) ABSTRACT

Antigenic polypeptides derived from a naturally occurring horn fly protein, and nucleic acid molecules encoding the polypeptides, are described. The polypeptides elicit an immune response which, in turn, produces detrimental effects in horn flies feeding on vaccinated cattle. Thus, the present disclosure provides a novel horn fly vaccine.

8 Claims, 5 Drawing Sheets

Specification includes a Sequence Listing.

SEQUENCE LISTING

<160> NUMBER OF SEQ ID NOS: 4

<210> SEQ ID NO 1
<211> LENGTH: 413
<212> TYPE: PRT
<213> ORGANISM: Haematobia irritans

<400> SEQUENCE: 1

```
Met Gly Phe Ser Thr His Tyr Thr Cys Ala Leu Ile Leu Ala Ile Thr
1               5                   10                  15

Ile Cys Tyr Ala Ser Ser Ala Lys Leu Asn Met Asn His Ile Cys Ala
            20                  25                  30

Leu Val Asn Asp Gly Leu Met Ile Ser Ser Ala Ala Ser Cys Asp Thr
        35                  40                  45

Tyr Tyr Ala Cys Arg Gly Gly Lys Ala Thr Arg Gln Ile Cys Ala Pro
    50                  55                  60

Gly Tyr Phe Phe Asp Lys Glu Ile Gln Met Cys Ala Pro Gln Asp Gln
65                  70                  75                  80

Val Gln Cys Leu Ala Ala Asn Ala Pro Ala Cys Ser Gly Tyr Ser Leu
                85                  90                  95

Gly Glu Trp Ala Pro Val Met Gly Ser Cys Thr Asp Phe Tyr Tyr Cys
            100                 105                 110

Ser Thr Asn Gly Pro Leu Arg Ala Asn Cys Pro Asp Gly Glu Tyr Ala
        115                 120                 125

Ala Pro Thr Ile Gln Gln Cys Val Tyr Ala Ser Ser Tyr Asn Cys Met
    130                 135                 140

Gln Ser Ala Ala Pro Ala Pro Pro Ser Ser Gly Glu Ser Thr Asp Ser
145                 150                 155                 160

Leu Gly Asp Glu Val Val Glu Asp Val Asp Leu Thr Val Pro Val Asn
                165                 170                 175

Met Cys Ile Phe Ile Gln Ser Gly Ile Phe Phe Ala Ser Ala Asp Ala
            180                 185                 190

Cys Thr Ser Trp Asn Lys Cys Glu Asn Gly Val Met Ile Asp Gly Ile
        195                 200                 205

Cys Pro Asn Gly Leu Glu Tyr Asn Val Ile Thr Met Ser Cys Ala Tyr
    210                 215                 220

Pro Ser Ser Val Thr Cys Ser Gln Val Thr Asn Asp Pro Asn Leu Ile
225                 230                 235                 240
```

```
Pro Ala Ala Thr Cys Thr Thr Lys Asn Ala Ile Lys Ala Gly Pro Thr
                245                 250                 255

Cys Asp Thr Tyr Met Val Cys Asp Gly Ser Thr Tyr Gln Leu Thr Gln
            260                 265                 270

Cys Pro Ser Gly Glu Tyr Phe Asp Thr Val Ser Gln Thr Cys Val Asp
        275                 280                 285

Arg Leu Asp Ala Arg Asn Asn Cys Asp Arg Cys Glu Gly Thr Thr Lys
    290                 295                 300

Ala Phe Val Asn Met Tyr Ser Ala Ser Asn Cys Thr Gly Tyr Leu Tyr
305                 310                 315                 320

Cys Val Asn Gly Ala Glu Ala Ser Ser Gly Tyr Cys Thr Asp Gly Ser
                325                 330                 335

Tyr Phe Asp Glu Ala Glu Gly Ala Cys Val Arg Gly Glu Ser Glu Pro
            340                 345                 350

Leu Tyr Gly Cys Cys Asn Pro Lys Tyr Phe Asn Asn Ser Ser Ser Asp
        355                 360                 365

Ser Ser Asn Thr Thr Glu Ala Asp Asp Glu Thr Thr Asp Gly Glu Thr
    370                 375                 380

Ala Asp Ala Asp Ala Asp Ser Asn Val Thr Thr Asp Ser Asp Asp Gly
385                 390                 395                 400

Ala Thr Thr Glu Ser Gly Ser Gly Ala Thr Thr Asp Ala
                405                 410

<210> SEQ ID NO 2
<211> LENGTH: 391
<212> TYPE: PRT
<213> ORGANISM: Artificial Sequence
<220> FEATURE:
<223> OTHER INFORMATION: Chemically Synthesized

<400> SEQUENCE: 2

Ala Lys Leu Asn Met Asn His Ile Cys Ala Leu Val Asn Asp Gly Leu
1               5                   10                  15

Met Ile Ser Ser Ala Ala Ser Cys Asp Thr Tyr Tyr Ala Cys Arg Gly
                20                  25                  30

Gly Lys Ala Thr Arg Gln Ile Cys Ala Pro Gly Tyr Phe Phe Asp Lys
            35                  40                  45

Glu Ile Gln Met Cys Ala Pro Gln Asp Gln Val Gln Cys Leu Ala Ala
        50                  55                  60

Asn Ala Pro Ala Cys Ser Gly Tyr Ser Leu Gly Glu Trp Ala Pro Val
65                  70                  75                  80

Met Gly Ser Cys Thr Asp Phe Tyr Tyr Cys Ser Thr Asn Gly Pro Leu
                85                  90                  95

Arg Ala Asn Cys Pro Asp Gly Glu Tyr Ala Ala Pro Thr Ile Gln Gln
            100                 105                 110

Cys Val Tyr Ala Ser Ser Tyr Asn Cys Met Gln Ser Ala Ala Pro Ala
        115                 120                 125

Pro Pro Ser Ser Gly Glu Ser Thr Asp Ser Leu Gly Asp Glu Val Val
    130                 135                 140

Glu Asp Val Asp Leu Thr Val Pro Val Asn Met Cys Ile Phe Ile Gln
145                 150                 155                 160

Ser Gly Ile Phe Phe Ala Ser Ala Asp Ala Cys Thr Ser Trp Asn Lys
                165                 170                 175

Cys Glu Asn Gly Val Met Ile Asp Gly Ile Cys Pro Asn Gly Leu Glu
            180                 185                 190
```

```
Tyr Asn Val Ile Thr Met Ser Cys Ala Tyr Pro Ser Ser Val Thr Cys
            195                 200                 205

Ser Gln Val Thr Asn Asp Pro Asn Leu Ile Pro Ala Ala Thr Cys Thr
        210                 215                 220

Thr Lys Asn Ala Ile Lys Ala Gly Pro Thr Cys Asp Thr Tyr Met Val
225                 230                 235                 240

Cys Asp Gly Ser Thr Tyr Gln Leu Thr Gln Cys Pro Ser Gly Glu Tyr
                245                 250                 255

Phe Asp Thr Val Ser Gln Thr Cys Val Asp Arg Leu Asp Ala Arg Asn
            260                 265                 270

Asn Cys Asp Arg Cys Glu Gly Thr Thr Lys Ala Phe Val Asn Met Tyr
        275                 280                 285

Ser Ala Ser Asn Cys Thr Gly Tyr Leu Tyr Cys Val Asn Gly Ala Glu
290                 295                 300

Ala Ser Ser Gly Tyr Cys Thr Asp Gly Ser Tyr Phe Asp Glu Ala Glu
305                 310                 315                 320

Gly Ala Cys Val Arg Gly Glu Ser Glu Pro Leu Tyr Gly Cys Cys Asn
                325                 330                 335

Pro Lys Tyr Phe Asn Asn Ser Ser Ser Asp Ser Ser Asn Thr Thr Glu
            340                 345                 350

Ala Asp Asp Glu Thr Thr Asp Gly Gly Thr Ala Asp Ala Asp Ala Asp
        355                 360                 365

Ser Asn Val Thr Thr Asp Ser Asp Asp Gly Ala Thr Thr Glu Ser Gly
370                 375                 380

Ser Gly Ala Thr Thr Asp Ala
385                 390

<210> SEQ ID NO 3
<211> LENGTH: 1242
<212> TYPE: DNA
<213> ORGANISM: Haematobia irritans

<400> SEQUENCE: 3
atgggtttct ctaccattta tacatgtgcc ttgattttgg ccataaccat ttgctatgca      60
tcttcagcca aattgaatat gaaccatatt tgtgctttgg ttaatgaygg tctaatgatt     120
tcctctgccg cwtcttgyga tacctattac gcttgycgtg gtggtaaggc cactcgtcaa     180
atctgtgctc caggctattt cttcgayaaa gaaattcaaa tgtgtgcccc ccaagatcaa     240
gttcaatgtt tggccgccaa tgctcctgcc tgttcgggat actcattggg cgaatgggct     300
ccagtaatgg gttcctgtac agatttctat tattgcagta ctaatggtcc attgcgtycc     360
aattgtccag atggagagta ttycawtcct accatacaac agtgcgtcta tgccagttca     420
tataattgca tgcaatcggc cgcaccagct ccaccaagca gcggtgagag tacggacagt     480
ttgggagatg aggttgtgga agatgtcgat ctaacagtgc ctgtgaatat gtgtattttc     540
attcaaagtg gaatattctt tgccagcgcc gacgcatgta catcatggaa taaatgtgaa     600 atggtgtaa tgattgatgg aatctgtccc aatggcttgg aatacaatgt tattactatg     660
tcatgtgctt atccttcaag tgttacctgt tcccaggtta ccaatgatcc caacttaatt     720
ccagccgcca cctgtaccac caaaaatgcc attaaggccg gtcccacttg tgatacttat     780
atggtatgtg atggctccac ttaccaactc actcaatgtc caagtggtga atatttcgat     840
actgtcagtc aaacctgtgt agatcgtttg gatgctcgta caattgcga tcgttgcgag     900 ggcaccacaa aggcctttgt taacatgtay tcggccagca attgcactgg atatttgtat     960
```

```
tgtgtaaatg gtgcagaagc ctcatcggga tattgtactg acggtagcta tttcgatgaa    1020
gctgagggtg cttgtgtcag gggtgaaagc gaacctcttt atggttgctg taatcctaaa    1080
tatttcaaca atagctccag cgatagctcc aataccacag aggctgatga tgaaacaacc    1140
gatggcgaaa catytgatgc agattytgat tcaaatgtga caacagattc tgatgatggt    1200
gctaccactg aaagtggatc tggagccaca acagatgctt aa                       1242
```

<210> SEQ ID NO 4
<211> LENGTH: 1260
<212> TYPE: DNA
<213> ORGANISM: Artificial Sequence
<220> FEATURE:
<223> OTHER INFORMATION: Chemically Synthesized

<400> SEQUENCE: 4

```
atgggttttt ctacacatta cacttgcgca ttgattcttg ctattactat ctgttatgca      60
tcttccgcta agctgaacat gaaccacatc tgtgctctgg ttaacgacgg tctgatgatc     120
tcaagtgctg cctcctgtga tacatactat gcttgcagag gtggaaaggc cactagacag     180
atatgtgcac ctggatactt tttcgacaaa gaaatccaaa tgtgtgctcc acaagatcag     240
gttcaatgct tagcagctaa tgccccagca tgttccggtt attcactggg agagtgggcc     300
cctgtcatgg gttcatgtac tgactttttac tattgcagta ccaacggacc tttgagagct     360
aattgtcccg atggtgaata cgccgcacct actattcaac agtgcgtgta cgcatcttcc     420
tataactgta tgcagtctgc tgccccagct ccaccttcaa gtggagagag taccgactct     480
ttgggagatg aagttgtcga ggatgttgac cttacagtgc cagtaaacat gtgtattttc     540
attcaatccg gtattttctt tgcttcagcc gacgcatgta ctagttggaa caaatgcgaa     600
aatggtgtta tgatcgatgg aatatgtccc aacggtttag agtacaatgt catcactatg     660
tcctgcgctt atccatcttc cgttacctgt tcacaggtca caaacgatcc caacttgatt     720
ccagcagcta cttgtactac caagaacgcc atcaaagcag gacctacctg tgacacatac     780
atggtttgcg atggttctac ttatcagttg acccaatgcc catcaggaga atactttgat     840
actgtttctc aaacttgtgt agacagactt gatgctagaa caattgtgaa tagatgcgag     900
ggtacaacta aggctttcgt gaacatgtat tccgcctcaa attgtactgg atacttgtat     960
tgcgtaaacg gtgctgaagc ctcaagtgga tactgcaccg acggttctta ttttgatgaa    1020
gctgagggag cctgtgtcag aggtgaatcc gagccacttt acggatgttg caaccctaaa    1080
tatttcaaca attcttcctc agacagttct aataccacag aagctgatga cgagactacc    1140
gatggtgaaa ctgcagatgc tgacgccgat tctaatgtta caactgactc cgatgacgga    1200
gctaccacag agagtggttc tggagccact accgatgcac atcaccatca ccatcactga    1260
```

HORN FLY PROTEIN AS ACTIVE ANTIGEN IN ANTI-HORN FLY VACCINE FOR PROTECTION OF BOVINES AGAINST HORN FLY INFESTATIONS

BACKGROUND OF THE INVENTION

Field of Invention

Antigenic polypeptides derived from a naturally occurring horn fly protein, and nucleic acid molecules encoding the polypeptides, are described. The polypeptides elicit an immune response which, in turn, produces detrimental effects in horn flies feeding on vaccinated cattle. Thus, the present disclosure provides a novel horn fly vaccine.

Background

The horn fly, *Haematobia irritans irritans*, causes significant production losses to the cattle industry where it occurs. Horn fly control relies on insecticides; however, alternative control methods such as vaccines are needed due to the fly's capacity to quickly develop resistance to insecticides, and the pressure for eco-friendly options.

The horn fly, *Haematobia irritans irritans* (Diptera: Muscidae) (Linnaeus, 1758), is present in central and southern Europe, Asia Minor, North Africa and the Americas (Oyarzún et al, Med. Vet. Entomol., (2008)22:188-202). Large populations of this fly can cause significant blood loss and annoyance, which in turn reduce milk production, weaning weight, and weight gain, resulting in economic losses estimated at $876 million and $2.56 billion per year in the US (Kunz et al, "Estimated losses of livestock to pests." In: Pimental D, editor. CRC Handbook of Pest Management in Agriculture. Boca Raton, Fla.: CRC Press; 1991. p. 69-98) and Brazil (Grisi et al, Rev. Bras. Parasitol. Vet., (2014) 23:150-6), respectively. The horn fly's high biotic potential, short life cycle, large number of generations per year, and close association to its host, combined with the intensive use of insecticides have contributed to the quick selection of populations resistant to most of the products commercially available in the US, including organochlorines (DDT), organophosphates, pyrethroids, and cyclodienes (endosulfan) (Oyarzún et al, supra; Georghiou, G. P., Phytoprotection (1994) 754:51-9; Domingues et al, J. Med. Entomol. (2014) 51:964-970). Due to their long-lasting effects, which reduces the need for insecticide treatments; lack of residue in animal-derived products or the environment; high specificity with no side-effects on non-target species; and low probability of selecting resistant populations, vaccines could be a valuable option for horn fly control (Willadsen, P., Vet. Parasitol., (1997) 71:209-22; Pruett, J. H., Int. J. Parasitol., (1999) 29:25-32).

There is no anti-horn fly vaccine available commercially, and there is limited research published on this topic. A vaccine containing 1 mg of crude antigen extracted from horn fly intestine plus Freund's Incomplete and *Lactobacillus casei* adjuvants affected oviposition but not fly survival (Bautista, et al, Ann. NY Acad. Sci., (2004) 1026:284-8). Flies that fed upon animals immunized with recombinant thrombostasin, an anti-thrombin peptide found in horn fly saliva, had a smaller blood meal and delayed egg development when compared with flies fed on non-vaccinated cattle (Cupp et al, Vaccine, (2004) 22:2285-97; Cupp et al, J. Med. Entomol., (2010) 47:610-17). Experimental vaccination with recombinant hematobin, a salivary protein, increased the cattle's anti-hematobin IgG response and reduced fly loads by about 30% compared with the control group (Breijo et al, J. Econ. Entomol., (2017) 110:1390-3).

Very few anti-arthropod vaccines have been developed and only a single vaccine has successfully and sustainably reached the global market. Allen and Humphreys (Nature, (1979) 280:491-3) immunized mammalian hosts with protein extracts from partially fed ticks and discovered that ticks feeding upon the vaccinated hosts showed significantly reduced reproductive performance. Willadsen et al. (Int. J. Parasitol., (1988)18:183-9) discovered the tick protein Bm86 was an effective antigen as a component of an anti-tick vaccine, leading to the anti-tick vaccine TickGARD (Willadsen et al, Parasitol., (1995) 110(S1):S43-50), soon followed by the anti-tick vaccine GAVAC (Canales et al, Vaccine (1997) 15:414-22).

Considering the economic losses caused by *H. irritans* to the cattle industry, and the fly's resistance to current chemical control methods, novel technologies are needed to help control this pest. As detailed herein, we have developed an anti-horn fly vaccine using a novel antigen to meet this pressing need.

SUMMARY OF THE INVENTION

In one embodiment, the present disclosure provides a synthetic polypeptide having an amino acid sequence at least 95% identical to SEQ ID NO: 1 or SEQ ID NO: 2. In some embodiments, this synthetic polypeptide has the exact amino acid sequence of SEQ ID NO: 1 or SEQ ID NO: 2. In other embodiments, the synthetic polypeptides disclosed herein are combined with a pharmaceutically acceptable carrier.

An additional embodiment provided by the present disclosure is an isolated nucleic acid molecule encoding the synthetic polypeptides described. In specific embodiments, this nucleotide has the nucleotide sequence of SEQ ID NO: 3 or SEQ ID NO: 4. The present disclosure also provides a vector containing such a nucleic acid.

In still another embodiment, the present disclosure provides a method of eliciting an immune response against horn flies in a subject, comprising administering to the subject a composition comprising one or more of the synthetic polypeptides described herein, thereby eliciting an immune response to horn flies. In specific embodiments, the synthetic polypeptide utilized has the sequence of SEQ ID NO: 1 or SEQ ID NO: 2. In some embodiments, the composition with the synthetic polypeptide also contains a pharmaceutically acceptable carrier. In additional embodiments, the composition with the synthetic polypeptide further contains an adjuvant. In still other embodiments, the method has the additional step of administering the composition a second time.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

The novel features of the invention are set forth with particularity in the claims. Features and advantages of the present invention are referred to in the following detailed description, and the accompanying drawings of which:

(FIG. 1A) Adult flies in cages feeding for 10 days upon whole blood collected on Days 21, 42, 56 from animals vaccinated with BI-HS009 or buffer plus adjuvant only. (FIG. 1B) Egg collection by allowing oviposition onto moistened filter pads. (FIG. 1C) Fly eggs on filter paper. (FIG. 1D) Larval feeding cups containing manure. (FIG. 1E) Pupae recovered by washing manure onto sieves of different sizes. (FIG. 1F) Pupae recovered by flotation in a container filled with tap water.

DETAILED DESCRIPTION OF THE INVENTION

Figure 1A:
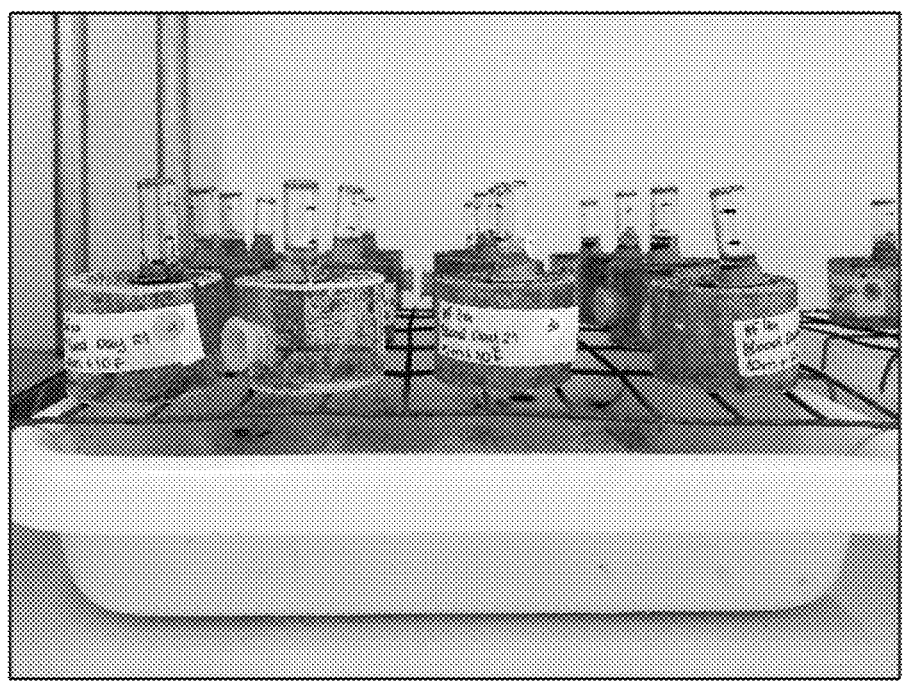
FIG. 1A-FIG. 1F provide pictorial representation of the horn fly in vitro feeding trial.

Presented herein is development and analysis of a novel horn fly vaccine based on a protein antigen. Numerous candidates were computationally and manually inspected, looking at predicted protein function, localization within the cell, solubility, life stage and organ of expression in Dipterans (when available), lack of amino acid similarity to mammalian proteins, presence in Diptera databases, and 10 candidates were selected for recombinant expression in *P. pastoris*.

To the best of our knowledge, attempts to develop an anti-horn fly vaccine have been restricted to studies with crude antigens extracted from horn fly's gut, recombinant thrombostasin (an anti-clotting protein found in horn fly saliva), and hematobin (a salivary gland protein) (Bautista et al, supra; Cupp et al, (2004), supra; Cupp et al, (2010), supra; Breijo et al, supra). However, only one showed a direct effect on fly infestation, but no direct negative effects on fly mortality, as also observed with the novel vaccine provided herein. The present study was the first to measure the effects of vaccination on different life stages of horn fly (adults, eggs and pupae) and to show that a significant IgG response was still observed in the vaccinated animals more than two months after the third vaccination when compared with the control group.

Preferred embodiments of the present invention are shown and described herein. It will be obvious to those skilled in the art that such embodiments are provided by way of example only. Numerous variations, changes, and substitutions will occur to those skilled in the art without departing from the invention. Various alternatives to the embodiments of the invention described herein may be employed in practicing the invention. It is intended that the included claims define the scope of the invention and that methods and structures within the scope of these claims and their equivalents are covered thereby.

Technical and scientific terms used herein have the meanings commonly understood by one of ordinary skill in the art to which the instant invention pertains, unless otherwise defined. Reference is made herein to various materials and methodologies known to those of skill in the art. Standard reference works setting forth the general principles of recombinant DNA technology include Sambrook et al., "Molecular Cloning: A Laboratory Manual", 2d ed., Cold Spring Harbor Laboratory Press, Plainview, N.Y., 1989; Kaufman et al., eds., "Handbook of Molecular and Cellular Methods in Biology and Medicine", CRC Press, Boca Raton, 1995; and McPherson, ed., "Directed Mutagenesis: A Practical Approach", IRL Press, Oxford, 1991. Standard reference literature teaching general methodologies and principles of fungal genetics useful for selected aspects of the invention include: Sherman et al. "Laboratory Course Manual Methods in Yeast Genetics", Cold Spring Harbor Laboratory, Cold Spring Harbor, N.Y., 1986 and Guthrie et al., "Guide to Yeast Genetics and Molecular Biology", Academic, New York, 1991.

Any suitable materials and/or methods known to those of skill can be utilized in carrying out the instant invention. Materials and/or methods for practicing the instant invention are described. Materials, reagents and the like to which reference is made in the following description and examples are obtainable from commercial sources, unless otherwise noted.

As used in the specification and claims, use of the singular "a", "an", and "the" include plural references unless the context clearly dictates otherwise.

The terms isolated, purified, or biologically pure as used herein, refer to material that is substantially or essentially free from components that normally accompany the referenced material in its native state.

The term "about" is defined as plus or minus ten percent of a recited value. For example, about 1.0 g means 0.9 g to 1.1 g and all values within that range, whether specifically stated or not.

The term "a nucleic acid consisting essentially of", and grammatical variations thereof, means nucleic acids that differ from a reference nucleic acid sequence by 20 or fewer nucleic acid residues and also perform the function of the reference nucleic acid sequence. Such variants include sequences which are shorter or longer than the reference nucleic acid sequence, have different residues at particular positions, or a combination thereof.

The term "adjuvant" means a substance or vehicle that non-specifically enhances the immune response to an antigen. Adjuvants can include a suspension of minerals (alum, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides can also be used as adjuvants (for example, see U.S. Pat. Nos. 6,194,388; 6,207,646; 6,214,806; 6,218,371; 6,239, 116; 6,339,068; 6,406,705; and 6,429,199). Adjuvants also include biological molecules, such as costimulatory molecules.

The term "administer"/"administration" means any method of providing a subject with a substance, such as a therapeutic agent by any effective route. Exemplary routes of administration include, but are not limited to, injection (such as subcutaneous, intramuscular, intradermal, intraperitoneal, and intravenous), oral, intraductal, sublingual, rectal, transdermal, intranasal, vaginal and inhalation routes.

The terms "coding sequence" and "coding region" as used herein refer to nucleotide sequences and nucleic acid sequences, including both RNA and DNA, that encode genetic information for the synthesis of an RNA, a protein, or any portion of an RNA or protein.

The term "effective amount" of a composition provided herein refers to the amount of the composition capable of performing the specified function for which an effective amount is expressed. The exact amount required can vary from composition to composition and from function to function, depending on recognized variables such as the compositions and processes involved. An effective amount can be delivered in one or more applications. Thus, it is not possible to specify an exact amount, however, an appropriate "effective amount" can be determined by the skilled artisan via routine experimentation.

The term "BI-HS009" refers to the protein having the amino acid sequence of SEQ ID NO: 1, as well as truncated versions of that protein, such as SEQ ID NO:2. In context, this term can also refer to a nucleic acid sequence encoding the protein of SEQ ID NO: 1, SEQ ID NO: 2, or truncated versions thereof. Exemplary nucleic acids include SEQ ID NO: 3, or any version of SEQ ID NO: 3 with base substitutions that result in a protein with a sequence identical to SEQ ID NO: 1, SEQ ID NO: 2, or the truncated versions. SEQ ID NO: 4 is an exemplary modified nucleic acid (codon-optimized for expression in *P. pastoris*). These terms, in the appropriate context, can also refer to modified versions of these SEQ ID NOs, such as those comprising deletions, insertions, and other recombinant modifications.

The term "immunize" means to render a subject protected from an infectious disease, such as by vaccination.

The term "immune response" refers to a response of a cell of the immune system, such as a B-cell, T-cell, macrophage or polymorphonucleocyte, to a stimulus such as an antigen or vaccine. An immune response can include any cell of the body involved in a host defense response, including for example, an epithelial cell that secretes an interferon or a cytokine. An immune response includes, but is not limited to, an innate immune response or inflammation. As used herein, a protective immune response refers to an immune response that protects a subject from infection (prevents infection or prevents the development of disease associated with infection). Methods of measuring immune responses are well known in the art and include, for example, measuring proliferation and/or activity of lymphocytes (such as B or T cells), secretion of cytokines or chemokines, inflammation, antibody production and the like.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other is regarded as a position with non-identical residues. The alignment of the two sequences is performed by the Needleman and Wunsch algorithm (Needleman and Wunsch, J Mol Biol, (1970) 48:3, 443-53). A computer-assisted sequence alignment can be conveniently performed using a standard software program such as GAP which is part of the Wisconsin Package Version 10.1 (Genetics Computer Group, Madison, Wis., USA) using the default scoring matrix with a gap creation penalty of 50 and a gap extension penalty of 3.

The phrase "high percent identical" or "high percent identity", and grammatical variations thereof in the context of two polynucleotides or polypeptides, refers to two or more sequences or sub-sequences that have at least about 80%, identity, at least about 81%, 82%, 83%, 84%, 85%, 86%, 87%, 88%, 89%, 90%, 91%, 92%, 93%, 94%, 95%, 96%, 97%, 98%, 99%, or 100% nucleotide or amino acid identity, when compared and aligned for maximum correspondence, as measured using a sequence comparison algorithm or by visual inspection. In one exemplary embodiment, the sequences are high percent identical over the entire length of the polynucleotide or polypeptide sequences.

The term "cattle" can generally refer to any member of the Bovinae subfamily and includes domesticated and wild cows, bulls, yak, bison, and buffalo.

A "vaccine", or "immunogenic composition" is herein defined as a biological agent capable of providing a protective response in an animal to which it has been delivered but not capable of causing a serious disease in that animal. Thus, the vaccine of the present disclosure stimulates antibody production or cellular immunity against the target (e.g., horn fly), which, in turn, causes a detrimental effect on the target—such as decreased feeding, increased mortality, decreased oviposition, or other effects that lead to a lessening of effect on vaccinated subjects compared to a non-vaccinated group, or an increased effect on target organisms feeding on vaccinated subjects compared to non-vaccinated subjects.

The immunogenically effective amounts of immunogenic compositions disclosed herein can vary based upon multiple parameters. In general, however, effective amounts per dosage unit can be about 20-250 µg recombinant BI-HS009 protein, about 20-150 µg recombinant BI-HS009 protein, or about 50-100 µg recombinant BI-HS009 protein. An individual dose can contain 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 200, 205, 210, 215, 220, 225, 230, 235, 240, 245, 250 or more µg of recombinant BI-HS009 protein per dose. These amounts can also include antigenic portions of the full-length BI-HS009 protein.

One, two, or more dosage units can be utilized in practicing the methodologies of the present invention. If two dosage units are selected, then a first dose of vaccine can be applied in early spring when horn flies first appear on animals and again at about two or three weeks later. A dosage unit can readily be modified to fit a desired volume or mass by one of skill in the art. Regardless of the dosage unit parameters, immunogenic compositions disclosed herein can be administered in an amount effective to produce an immune response to the presented antigen (e.g., BI-HS009 protein). An "immunogenically effective amount" or "effective amount" of an immunogenic composition as used herein, is an amount of the composition that provides sufficient levels of antigenic protein to produce a desired result, such as induction of, or increase in, production of antibody specific to the antigen, protection against horn fly feeding, adult mortality while feeding, decrease in number of eggs produced, decrease in number of larvae, decrease in number of pupae, and decrease in adult emergence and the subsequent population. Amounts of immunogenic compositions capable of inducing such effects are referred to as an effective amount, or immunogenically effective amount, of the immunogenic compositions.

Dosage levels of active ingredients (e.g., BI-HS009 protein) in immunogenic compositions disclosed herein, can be varied by one of skill in the art to achieve a desired result in a subject or per application. As such, a selected dosage level can depend upon a variety of factors including, but not limited to, formulation, combination with other treatments, severity of a pre-existing condition, and the presence or absence of adjuvants. In preferred embodiments, a minimal dose of an immunogenic composition is administered. As used herein, the term "minimal dose" or "minimal effective dose" refers to a dose that demonstrates the absence of, or minimal presence of, toxicity to the recipient, but still results in producing a desired result (e.g., protective immunity). Minimal effective doses, or minimum immunizing doses, of the recombinant immunogenic compositions provided herein can include about 20-250 μg recombinant BI-HS009 protein, about 20-150 μg recombinant BI-HS009 protein, or about 50-100 μg recombinant BI-HS009 protein. The minimal effective doses can also be any dose within the range of 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 200, 205, 210, 215, 220, 225, 230, 235, 240, 245, 250 or more μg of recombinant BI-HS009 protein per dose. These amounts can also include antigenic portions of the full-length BI-HS009 protein. Determination of a minimal dose is well within the capabilities of one skilled in the art.

Formulations and Administration

Dosage levels of active ingredients in vaccines disclosed herein, can be varied by one of skill in the art to achieve a desired result in a subject or per application. As such, a selected dosage level can depend upon a variety of factors including, but not limited to, formulation, combination with other treatments, and the presence or absence of adjuvants. In preferred embodiments, a minimal dose of an immunogenic composition is administered. Determination of a minimal dose is well within the capabilities of one skilled in the art.

A vaccine or immunostimulatory composition provided herein comprises an antigenic protein provided herein (e.g., BI-HS009), and typically a pharmaceutically acceptable carrier or diluent customarily used for such compositions. Carriers include stabilizers, preservatives and buffers. Suitable stabilizers include, for example, SPGA (sucrose, phosphate, glutamate and albumin), carbohydrates (sorbitol, mannitol, starch, sucrose, dextran, glutamate, and glucose), proteins (dried milk, serum, albumin, casein), or degradation products thereof. Suitable buffers include, for example alkali metal phosphates. Preservatives that can be utilized, include, but are not limited to, thimerosal, merthiolate and gentamicin. Diluents include water, aqueous buffers (e.g., buffered saline, phosphate buffered saline), alcohols and polyols (e.g., glycerol).

In some instances, vaccines of the present invention also contain or comprise one or more adjuvants, which includes any material included in the immunogenic composition formulation that enhances an immune response in the recipient that is induced by the immunogenic composition. Other adjuvants can be included as an extra component of the immunogenic compositions, and include such categories as aluminum salts (alum), oil emulsions, saponins, immune-stimulating complexes (ISCOMs), liposomes, microparticles, nanoparticles, nonionic block copolymers, derivatized polysaccharides, cytokines, and a wide variety of bacterial derivatives. Any relevant adjuvant known in the art can be utilized in practicing the inventions disclosed herein. Factors influencing the selection of an adjuvant include animal species, specific pathogen, antigen, route of immunization, and type of immunity needed and can be readily determined by one of skill in the art.

Immunogenic compositions of the present disclosure can also comprise carriers in addition to the immunogenic protein(s). Carriers utilized in practicing the immunogenic compositions provided herein can be any known in the art and can be liquid, solid, semi-solid, or gel. The type of formulation can be modified depending on the route of administration of the antigen. Preferably, carriers are non-toxic to the recipient. One of skill in the art is readily able to choose such carriers for application to recipient animals such as poultry.

Vaccines provided herein may be administered by intramuscular, subcutaneous, intranasal or injection routes in an amount which is effective to produce an immune response (humoral and/or cellular) to the antigenic protein (e.g., BI-HS009). The vaccine may be administered orally, through direct oral inoculation, dosed in drinking water, or though bait delivery systems. The effective amount of the protein may vary according to parameters considered by those skilled in the art. Effective amounts can be experimentally determined as necessary by those of skill in the art by following any known method or the guidance provided in the Examples herein.

Having generally described this invention, the same will be better understood by reference to certain specific examples, which are included herein to further illustrate the invention and are not intended to limit the scope of the invention as defined by the claims.

EXAMPLES

Example 1

Antigen Characterization

Following horn fly transcriptome in silico analysis of over 79,500 horn fly open reading frames, ten (10) antigens were selected for in vitro characterization and expression. To evaluate if the 10 vaccine candidate antigens selected for in vitro expression were present in adult horn flies, proteins were extracted from adult flies and analyzed by mass spectrometry. The adult flies used in the study were from the reference laboratory strain that has been kept in colony feeding upon citrated bovine blood at the USDA-ARS Knipling-Bushland U.S. Livestock Research Laboratory (KBUSLIRL) for over 50 years (Lohmeyer & Kammlah, Southwest Entomol., (2006) 31:83-5)

Aqueous- and urea-extractible proteins were extracted using the ReadyPrep Sequential Extraction Kit (Bio-Rad) following the manufacturer's recommendation with a few modifications. Briefly, two samples of 100 adult flies of mixed sex, from unfed and citrated blood fed populations were separately ground on ice with a disposable pestle for 30 s followed by 10 s centrifugation at 16,100 g, repeating this twice. Aqueous soluble proteins were extracted by adding Reagent 1 (40 mM Tris) (ReadyPrep Sequential Extraction Kit) (Bio-Rad, Hercules, Calif.) and FOCUS ProteaseArrest (G-Bioscience, St. Louis, Mo.) to the samples and grinding with a polytron (PCU-2-110) (Brinkmann Instruments, Westbury, N.Y.) for 10 seconds, returned to ice for 30 seconds, repeating this twice. Ribonuclease A from Bovine Pancreas (Sigma Aldrich, St. Louis, Mo.) was added and the samples incubated at room temperature for 45 min on an orbital shaker at 225 ppm. Subsequently, samples were centrifuged for 30 min at 16,100 g at room temperature and the supernatant was removed and saved as the Reagent 1 fraction, containing the aqueous-solubilized proteins. The pellet was washed three times using Reagent 1 plus FOCUS ProteaseArrest (G-Bioscience) and centrifuged for 30 min at 16,100 g at room temperature. The supernatant was discarded after each centrifugation and, after the final wash, the pellet was resuspended with Reagent 2 (8 M urea, 4% w/v CHAPS, 40 mM Tris, 0.2% w/v Bio-Lyte 3/10 ampholyte)+ tributyl phosphine (TBP) (ReadyPrep Sequential Extraction Kit) (Bio-Rad), followed by incubation at room temperature for 1 h shaking at 225 rpm and centrifugation as previously described. This supernatant was recovered as the Reagent 2 fraction, containing the 8M urea-solubilized proteins.

Reagent 1 and 2 fractions were analyzed by SDS-PAGE under denaturing conditions using 1× Tris/Glycine/SDS Buffer (Bio-Rad) and 4% acrylamide (AA)/bis-acrylamide (bis) stacking gel and 12% AA/bis resolving gel. Gels were stained using Coomassie Brilliant Blue R-250 (Bio-Rad), manually cut, and pieces containing proteins of 10-~250 kDa were used in the mass spectrometry analysis.

Mass spectrometry was performed at the Department of Chemistry of the University of Georgia. Briefly, the gel pieces were digested with trypsin and a list of precursor ions was generated from the provided protein sequences. The mass-to-charge values (m/z) of theoretical tryptic peptides of these proteins with up to one missed cleavage and multiple possible charges were calculated to make up a target ion list. Only the peptides with molecular weights between 0.5 to 3 kDa were included in the target ion list. Using this target ion list, a customized MS acquisition method was generated for the LC/MS runs. During the LC/MS run, a survey MS scan measured all ions from m/z 350-1800 and generated a peak list. The computer matched the peak list of the survey scan in the target ion list. The most intense eight peaks were analyzed by MS/MS and if no ions from the target ion list were observed, the program picked eight ions that had the highest chance to produce good MS/MS spectra. Once those ions were analyzed by MS/MS, the program found the next possible candidates by doing another MS survey scan and looking at the peaks that were eluting, repeating the cycle described above. The LC/MS data were searched against the NCBI protein database (4,837 horn fly sequences as of Jan. 8, 2018) and the translated ORFs used in the in silico analysis using Mascot (Matrix Sciences, Boston, Mass.) combined with Proteome Discoverer (ThermoFisher Scientific, Carlsbad, Calif.).

The protein of SEQ ID NO: 1 (also referred to herein by the term "BI-HS009) was not detected in either the aqueous- or the 8 M urea-solubilized adult fly protein extracts, indicating the protein in adult flies is present in an extractable amount below or above the detection limit of the LC/MS, or the protein requires extraction solvents harsher than 8 M urea.

mRNA Transcript Analysis

In order to check if the mRNA transcripts of the vaccine antigens that were expressed in vitro were expressed in field populations of the horn fly, we performed RT-PCR and DNA sequencing of adult flies from various populations sampled over the years and stored at −80° C. for preservation of nucleic acids. All fly samples were collected using sweep nets, transferred into a plastic collection tube, set into dry ice or quick frozen in liquid nitrogen.

Wild flies were collected at the LSU AgResearch Saint Gabriel research farm in the state of Louisiana in 2006. Total RNA was extracted from 50 female flies using the ToTALLY RNA kit (Ambion Inc., Austin, Tex.), followed by polyA RNA isolation using the MicroPoly(A)Purist Kit (Ambion Inc.) and cDNA synthetized using the SMART RACE cDNA Amplification kit (Clontech, Mountain View, Calif.) following the manufacturers' recommendations.

Flies from Rosepine (wild flies collected at the Rosepine LSU AgResearch farm in the state of Louisiana in 1998) and Super Resistant (a since discontinued laboratory strain fed upon a stanchioned steer at KBUSLIRL from 1996-2006, sampled in May 1998) were also used in the study. For these samples, total RNA was extracted from a pool of adult males and females (10 each) using Trizol Reagent/chloroform/isopropanol. Briefly, tubes containing the flies were immersed in liquid nitrogen, transferred into dry ice, and pulverized using a mini-pestle. One ml of Trizol Reagent (Ambion by Life Technologies, Carlsbad, Calif.) was added per 100 mg of tissue and mixed well with a mini-pestle, followed by incubation for 5 min at room temperature. Then, 0.2 ml of chloroform (Eastman Kodak Co., Rochester N.Y.) per 1 ml of Trizol Reagent was added and the tubes vortexed for 30 s and incubated for 3 min at room temperature. Subsequently, tubes were centrifuged for 15 min at 12,000 g and 4° C. The upper aqueous phase was recovered and 0.5 ml of isopropanol (Sigma Aldrich) added per 1 ml of Trizol Reagent. The samples were vortexed and incubated for 30 min at room temperature, followed by centrifugation for 10 min at 12,000 g and 4° C. The supernatant was discarded and the pellet rinsed with 1 ml of 75% ethanol (Pharmco, Brookfield, Conn.) per 1 ml of Trizol Reagent by vortexing. Samples were centrifuged for 5 min at 7,500 g and 4° C. twice and the supernatant discarded after each centrifugation. The remaining pellet was air dried for 5 min at room temperature and resuspended in 50 µl nuclease-free water (Ambion Inc.). Subsequently, the total RNA was DNAse-treated using the RNase-Free DNase Set (Qiagen, Hilden, Germany) and the RNeasy Mini Kit (Qiagen) following the manufacturer's recommendations. cDNA was synthetized using the RETROscript Kit (Invitrogen by Thermo Fisher Scientific, Vilnius, Lithuania) following the manufacturer's recommendations.

Amplifications were performed on 25 µl PCR reactions with 1 µl of cDNA, 1×Q5 Reaction Buffer (New England Biolabs), 200 µM of dNTPs (Applied Biosystems, Foster City, Calif.), 0.5 µM each of primers, 0.02 U/µl of Q5 Hot Start High-Fidelity DNA Polymerase (New England Biolabs), and 1×Q5 High GC Enhancer (New England Biolabs). Amplification was carried out using a DNA Engine preheated to 98° C. and programmed to 30 s at 98° C., followed by either 30 or 35 cycles of denaturation at 98° C. for 10 s, annealing at different temperatures depending on the primer pair for 30 s, and extension at 72° C. for 30 s. A final extension of 72° C. for 2 min was also included. The PCR product was purified by agarose gel electrophoresis, and the single products were extracted and purified using the QIAquick Gel Extraction Kit (Qiagen Inc., Valencia, Calif.) per manufacturer's protocols. DNA sequencing was performed by Retrogen Inc. (San Diego, Calif.), sequencing both strands to ensure accurate results. MacVector version 15.1.4 with Assembler (MacVector Inc., Cary, N.C.) was used for sequence assembly and nucleotide alignments.

Example 2

Recombinant Expression of Candidate Antigens in *Pichia pastoris*

The proteins selected for in vitro expression were contracted to Creative BioMart (Shirley, N.Y., USA) for cloning and recombinant expression in *P. pastoris*. Briefly, the recombinant DNA was synthetized using codons optimized for *P. pastoris* expression. Clones producing the recombinant proteins were grown in BMGY (1% yeast extract, 2% peptone, 100 mM potassium phosphate pH 6.0, 1.34% yeast nitrogen base with ammonium sulfate without amino acids, $4 \times 10^{-5}$% biotin, 1% glycerol) or BMMY (BMGY but substituting 0.5% methanol for the 1% glycerol) media for 96 h. Every 24 h, methanol was added to a final concentration of 1% to maintain induction. Cells were harvested by centrifugation 96 h post-induction. Recombinant proteins were purified making use of the 6X-histidine tag supplied by the vector sequence and $Ni^{2+}$-NTA resin with a binding buffer composed of phosphate buffered saline (PBS) (pH 7.5) and 10% glycerol. Wash and elution buffers were composed of 0, 30, 50, 200 and 4000 mM imidazole. The final product was suspended in PBS (pH 7.5) and 50% glycerol and stored at −20° C. A 1 mg quantity of each protein was targeted for the initial small-scale tests. Subsequently, a 10 mg large-scale expression was used to produce sufficient protein for the vaccine trial reported herein.

Out of the 10 protein ORFs chosen for expression in *P. pastoris*, only the protein of SEQ ID NO: 1 was scaled up to the 10 mg scale and moved forward to the immunization trial stage. The protein having the sequence of SEQ ID NO: 1 has sequence similarity to peritrophin-48 (predicted) of *S. calcitrans* (BlastX e-value=$7.60E^{-178}$), *M. domestica* (BlastX e-value=$8.04E^{-148}$) *D. obscura* (BlastX e-value=$6.99E^{-81}$) and other *Drosophila* spp. According to GO annotation, its molecular function, biological process, and cellular component were chitin binding, chitin metabolic process, and extracellular region, respectively. CDD annotation found the BI-HS009 protein contains chitin-biding domain type 2 and chitin biding peritrophin-A domains. The BI-HS009 protein has 224 strong B-cell epitopes (BepiPred 2.0) and 196 and 217 linear and flexible B-cell epitopes according to BCPred and FBCpred, respectively. The BI-HS009 protein has 97 (27 strong, 70 weak) and 177 T-cell epitopes according to NetMHC4.0 and IEDB, respectively.

We sought to verify if the corresponding transcript (SEQ ID NO: 3) could be detected in wild horn fly samples. We designed RT-PCR primers and sequencing primers to allow us to amplify and sequence at least 40% of the putative transcript corresponding to the coding sequence. The results of our sequencing showed that the BI-HS009 ORF and the alignments of the expected transcript sequence with our sequencing data showed almost 100% identity (data not shown).

Verification of Purified Recombinant Proteins

Prior to the immunization trials, we sought to characterize and re-verify the purified antigen solutions via PAGE, Western blotting, and N-terminal sequencing. For the SDS-PAGE, the recombinant protein was resolved in NuPAGE 4-12% Bis-Tris gels 1 mm×12 wells (Invitrogen by ThermoFisher Scientific) with IVIES Running Buffer (Invitrogen by ThermoFisher Scientific) under denaturing conditions. Gels were stained using Coomassie Brilliant Blue R-250 (Bio-Rad) and gel images were saved using Bio-Rad Gel Doc EZ Imager and Image Lab 3.0 Software (Bio-Rad).

For the Western blotting, after the SDS-PAGE, the recombinant protein was transferred to 0.45 µM nitrocellulose membranes (Novex by Life Technologies, Carlsbad, Calif.) and detection was performed using the Western Breeze Chromogenic Western Blot Immunodetection kit (Invitrogen by ThermoFisher Scientific) and anti-his(C-term)-HRP antibody (Novex by Life Technologies) following the manufacturer's recommendation.

Additionally, N-terminal sequencing was used to verify the expressed recombinant protein contained the correct amino acids. Briefly, the protein was resolved by SDS-PAGE as previously described, then transferred to Sequi-blot PVDF membranes (Bio-Rad) using a blotting buffer composed of 1×CAPS pH 11 (Sigma Aldrich) and 10% Methanol (Sigma Aldrich), and stained with Coomassie Brilliant Blue R-250. The membrane was shipped to the Molecular Structure facility, University of California (Davis, Calif.) where the protein was sequenced with the Procise 494 (2) (Applied Biosystems).

Figure 2:
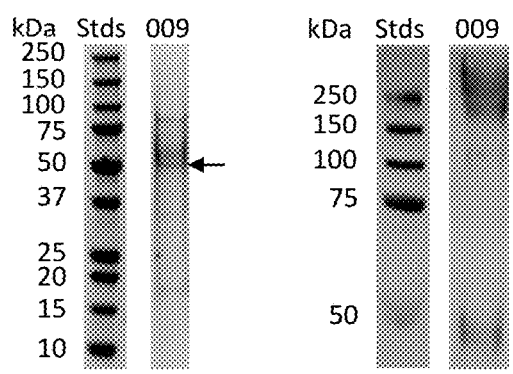
FIG. 2 provides pictorial representation of SDS-PAGE and Western blotting analysis of the BI-HS009 antigen candidate produced in *Pichia pastoris*. (Left) SDS-PAGE: 4.2 µg of BI-HS009 protein (SEQ ID NO: 2) were loaded and ran into NuPAGE 4-12% Bis-Tris gels, followed by staining with Coomassie Brilliant Blue R-250. Arrows indicate stained protein bands that were excised and subjected to N-terminal sequencing. (Right) Western blotting detection of BI-HS009 protein (SEQ ID NO: 2) using the Western Breeze Chromogenic Western Blot Immunodetection kit and anti-His tag antibodies. Stds=molecular weight standards (250 kDa-10 kDa).

The Coomassie stained protein in the gel (FIG. 2 (left)) and the anti-HisTag antibody-probed Western blotting (FIG. 2 (right)) had a higher molecular mass than the predicted 43.58 kDa of BI-HS009. We extracted the ~50 kDa band for N-terminal sequencing (FIG. 2) and the resulting 10 amino acids corresponded exactly to amino acids 23-33 of SEQ ID NO: 1. The first 22 amino acids of the BI-HS009 protein were predicted to function as a signal peptide by Creative Biomart and Vacceed and were predicted to be cleaved during expression and purification of BI-HS009, resulting in a protein having SEQ ID NO: 2. Thus, the N-terminal sequencing verified the scaled-up BI-HS009 protein was correctly expressed and purified.

Example 3

Immunogenicity and Immunization

All protocols for animal studies have been reviewed and approved by Boehringer Ingelheim's Institutional Care and Use Committee. An immunization trial was performed at the Missouri Research Center of Boehringer Ingelheim (Fulton, Mo.) to evaluate antigen immunogenicity and safety to cattle. Animals were housed on pastures and received water ad libitum as well as a grain supplement. Twelve Holstein cattle, >12 months old, were randomly distributed into two groups, BI-HS009 and control, which had eight and four animals, respectively. Animals from the BI-HS009 group were vaccinated subcutaneously with three doses of 114 µg/dose (4 ml dose) of BI-HS009 antigens in PBS (pH 7.5) plus 50% glycerol with adjuvant on Days 0, 21 and Day 42. The control group received a formulation containing only buffer and adjuvant (4 ml/dose) on the same days as the BI-HS009 group. The adjuvant used for all groups consisted of saponine, aluminum, and TS6 (Boehringer Ingelheim's proprietary adjuvant). Since the total dose contained a relatively large volume of adjuvant, the 4 mL dose was split and administered in two injection sites, one on each side of the animal at each vaccination time point.

Blood was collected before vaccination on Days 0, 21 and 42 as well as on Days 56, 70, 84, 98 and 112 using sodium heparin tubes (Becton, Dickinson and Company, Franklin Lakes, N.J.) for whole blood samples, and serum separator tubes for serum samples (Becton, Dickinson and Company). Serum samples were centrifuged, separated into aliquots and stored at −20° C. Whole blood tubes were kept refrigerated at 4° C. The serum and blood samples were shipped overnight to KBUSLIRL where they were subjected to ELISA or used for in vitro horn fly feeding, respectively.

Serological Analysis

The antibody response of each vaccinated animal was analyzed using an Indirect ELISA. Briefly, the recombinant protein used in the immunization trial was diluted in BupH Carbonate-Bicarbonate Buffer (ThermoFisher Scientific, Rockford, Ill.) to a final concentration of 0.25 µg/ml. One hundred µl of diluted antigen was added to each well of a 96 well plate (ThermoFisher Scientific) and the plate incubated overnight at room temperature. The wells were emptied and blocked with 300 µl of Blocker BLOTTO in TBS (ThermoFisher Scientific) for 1 h. Serum dilutions ranging from undiluted to 1:4000 were prepared in 1×TBS, 0.05% Tween 20, 10% Blocker BLOTTO (ThermoFisher Scientific) and added to each well and incubated for 1.5 h. The plate was then rinsed four times with 1×TBS Tween 20 Buffer (ThermoFisher Scientific) to remove unbound serum components, and 100 µl of Peroxidase Labeled Rabbit anti-Bovine IgG (H+L) (0.05 µg/ml) (KPL, Gaithersburg, Md.) added to each well, followed by 1 h incubation at room temperature. The plate was rinsed again four times with 1×TBS Tween 20 Buffer, and 100 µl of TMB (3,3',5,5'-Tetramethylbenzidine) substrate solution (ThermoFisher Scientific) added, followed by 20 min incubation. Finally, the reaction was stopped by adding 100 µl Stop Solution (ThermoFisher Scientific) and absorbance (OD450) read using an ELX800 plate reader (BioTek Instruments, Winooski, Vt.). Standards, samples and blanks were run in triplicates. The samples' antibody titers were expressed as antibody units determined relative to a standard curve (Miura et al, Vaccine, (2008) 26:193-200). Calculations were performed using the software Gen5, version 2.05 (BioTek Instruments).

The antibody response of each animal on each day measured by Indirect ELISA was log transformed and the means of each group were compared using Two-way ANOVA followed by Sidak multiple comparisons test. All the analyses were performed using GraphPad Prism version 8.2.1 for Windows (GraphPad Software, La Jolla Calif.) and differences were considered significant when $p<0.05$.

Figure 3:
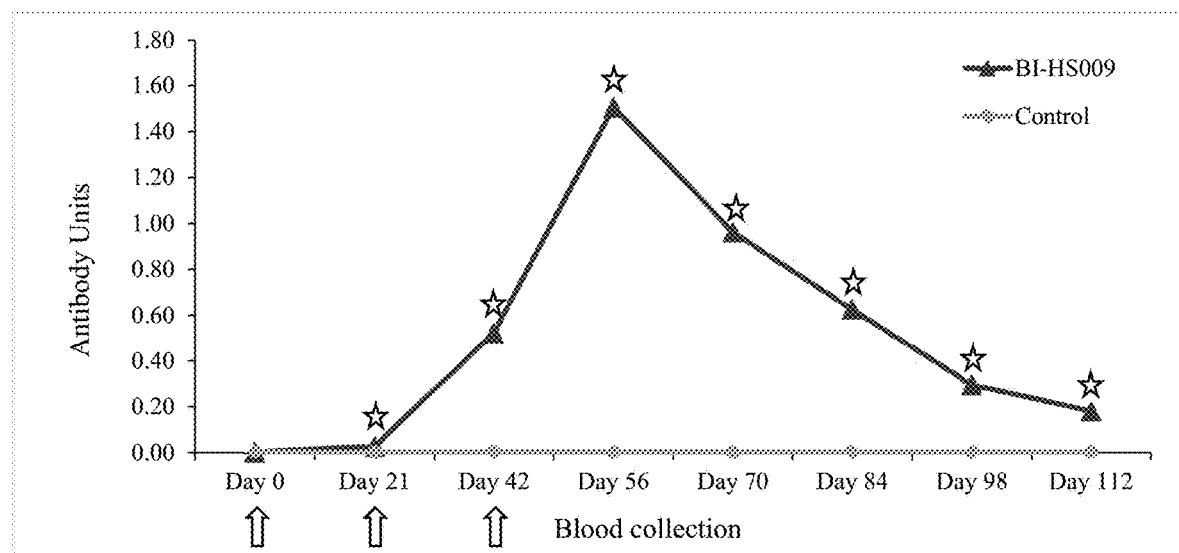
FIG. 3 provides pictorial representation of indirect ELISA results. Animals were vaccinated with either BI-HS009 (SEQ ID NO: 2) plus adjuvant (114 µg/dose, 4 ml dose) or buffer plus adjuvant only (Control), and blood collected just prior to vaccination on Days 0, 21 and 42, as well as every 2 weeks after the last vaccination until Day 112. Antibody titers are expressed as antibody units determined relative to a standard curve. Stars indicate significant difference ($p<0.05$) between the control and BI-HS009 (SEQ ID NO: 2) group according to Two-way ANOVA followed by Sidak multiple comparisons test. Arrows indicate vaccination days.

Animals from the control group that were vaccinated with buffer and adjuvant only, showed no cross-reacting antibody response to BI-HS009 in the ELISAs (FIG. 3). On the other hand, animals vaccinated with BI-HS009 had a specific IgG response, which was statistically different ($p<0.05$) from the control group starting at Day 21 until Day 112 for (FIG. 3). A peak in the immune response was observed on Day 56 and over 2 months after the final vaccination (Day 112), a statistically significant immune response was still evident in the vaccinated cattle (FIG. 3).

Protective Efficacy Against Horn Fly

The protective efficacy of the selected antigens was tested using an in vitro feeding assay performed at KBUSLIRL using one day old, unfed adult horn flies from the KBUSLIRL reference susceptible colony (Lohmeyer & Kammlah, supra). Blood samples from Days 21, 42 or 56 were used for the feeding trials and samples collected from all animals within a group (BI-HS009 or control) were pooled for each day. The blood was kept at 4° C. throughout the study.

The flies were kept in acrylic screened cages (4.8 cm diameter, 4.5 cm height) with a 1.25 cm access hole closed with #5 cap plugs (Protective Closures Co., Buffalo, N.Y.) (FIG. 1A). Four cages with 20 flies each (10 males and 10 females) were used per group (BI-HS009 and control) for each blood collection date (Days 21, 42 or 56).

Figure 1B:
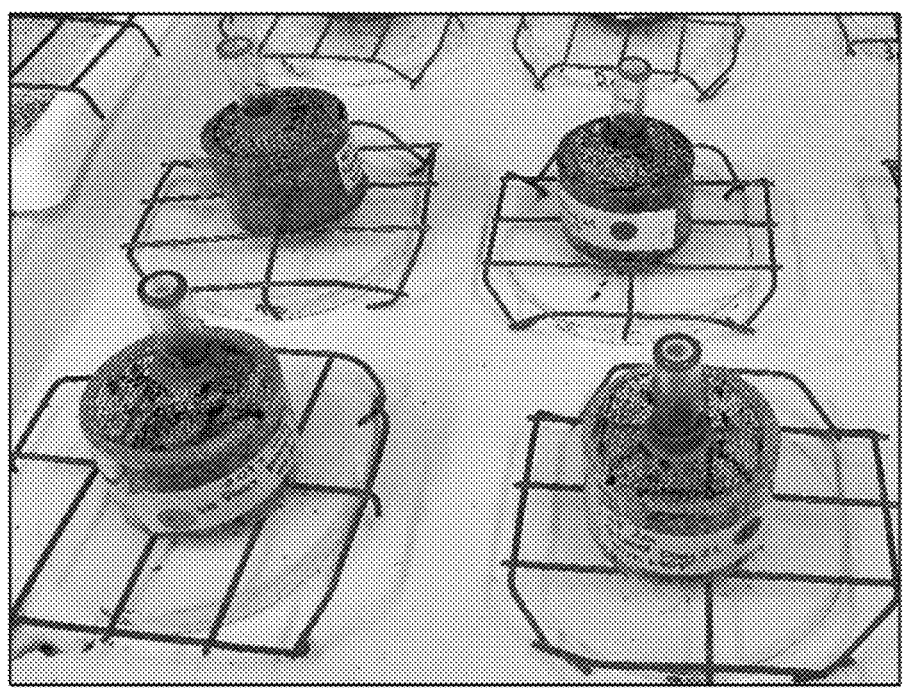
Figure 1C:
Figure 1D:
Figure 1E:
Figure 1F:
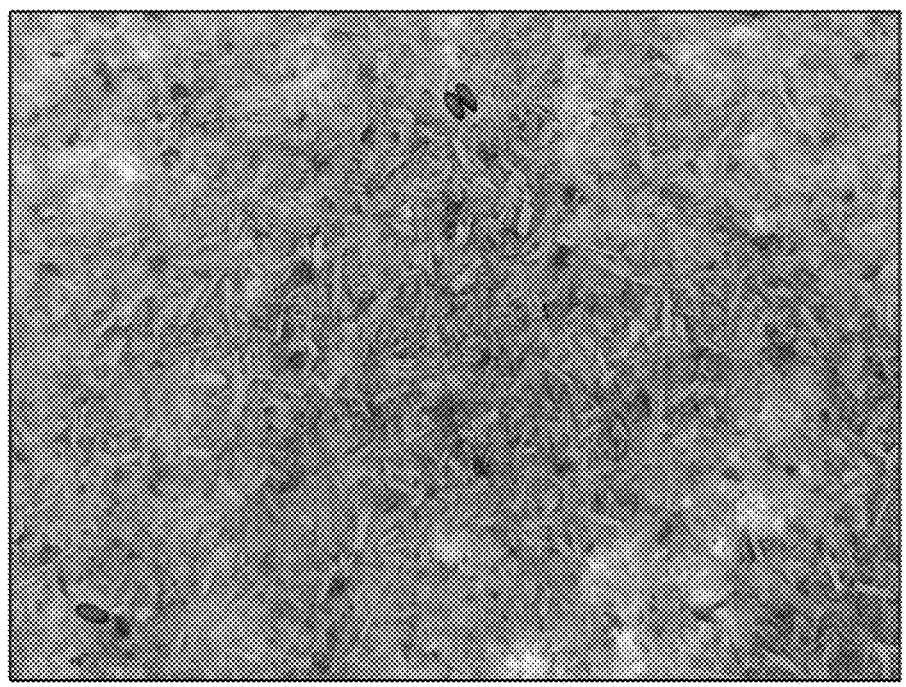

Flies were fed twice a day: glass vials (12×35 mm, 0.5 dram) (Kimble, China) containing 0.5 ml of blood were placed on top of the cages at 9 am each day and then replaced at 3 pm with 1.5 ml of fresh blood (FIG. 1A, FIG. 1B). Dead flies were recovered from cages daily and the number recorded. On days 6, 7 and 8, eggs were collected by setting cages atop a Whatman Filter Paper 1 Quantitative 90 mm diameter circle (Whatman International, Maidstone, England) placed onto a water-soaked all-natural cotton classic contour pad (Maxim Hygiene, New York) set in a 15×100 mm petri dish (Falcon, Durham, N.C.). A wire rack was placed on top of the filter paper/cotton pad/petri dish configuration to elevate the cage above the wet materials, and the cage with flies placed on top of the wire rack (FIG. 1B). Eggs were collected for 3 h, then counted with the aid of a magnifying glass (FIG. 1C) and placed in plastic cups (18 oz.) (Solo Cup Company, Lake Forest, Ill.) containing 100 g of cow manure. The cups were covered with tissue paper (LC Industries, Durham, N.C.) secured with rubber bands (size 54) (Skilcraft, Utica, N.Y.) and incubated at 29° C. (FIG. 1D). On Days 13, 14 and 15 pupae were recovered from the manure with the aid of two sieves, number 7 (2.80 mm) and number 20 (850 µm) (W. S. Tyler, Mentor, Ohio) (FIG. 1E) followed by flotation in a container filled with tap water (FIG. 1F), and placed in Petri dishes (100×15 mm) (Falcon) lined with a Whatman Filter Paper 1 Quantitative 90 mm diameter circle (Whatman International). The number of adults that emerged from the pupae were counted on Days 17, 18, 19.

The results of the in vitro feeding assays, including adult fly mortality while feeding, number of eggs, number of pupae, and adult emergence were analyzed using Two-way ANOVA with the Geisser-Greenhouse correction followed by Dunnett's multiple comparisons. All the analyses were performed using GraphPad Prism version 8.2.1 for Windows (GraphPad Software, La Jolla Calif.) and differences were considered significant when $p<0.05$.

Looking at adult mortality while feeding, number of eggs, number of pupae, and eventual adult emergence, at Day 56, flies feeding upon blood from cattle vaccinated with BI-HS009 produced 37% and 43% of the pupae and emerging adults, respectively, produced by flies feeding upon blood from cattle vaccinated with adjuvant only, a significant difference ($p<0.05$) (Table 1). No difference was observed for any of the parameters evaluated at the previous time points (Table 1). In Table 1, the asterisk indicates significant difference at $p<0.05$ between BI-HS009 and control group according to Two-way ANOVA with the Geisser-Greenhouse correction followed by Dunnett's multiple comparisons.

TABLE 1

| Efficacy results | | | | | |
|---|---|---|---|---|---|
| BI-HS009 | Cage 1 | Cage 2 | Cage 3 | Cage 4 | Mean (SD) |
| Adult mortality | | | | | |
| Day 21 | 1 | 0 | 2 | 3 | 1.50 (1.29) |
| Day 42 | 1 | 1 | 2 | 0 | 1.00 (0.82) |
| Day 56 | 2 | 0 | 1 | 2 | 1.25 (0.96) |
| Number of eggs | | | | | |
| Day 21 | 56 | 43 | 30 | 4 | 33.3 (22.2) |
| Day 42 | 70 | 34 | 27 | 64 | 48.8 (21.4) |
| Day 56 | 56 | 17 | 23 | 18 | 28.5 (18.5) |
| Number of pupae | | | | | |
| Day 21 | 46 | 33 | 23 | 4 | 26.5 (17.7) |
| Day 42 | 49 | 23 | 27 | 56 | 38.8 (16.2) |
| Day 56 | 43 | 13 | 21 | 18 | 23.8 (13.3)* |

TABLE 1-continued

Efficacy results

Number of emerging adults

| | Cage 1 | Cage 2 | Cage 3 | Cage 4 | Mean (SD) |
|---|---|---|---|---|---|
| Day 21 | 41 | 19 | 20 | 3 | 20.8 (15.6) |
| Day 42 | 25 | 11 | 7 | 40 | 20.8 (15.0) |
| Day 56 | 43 | 13 | 18 | 18 | 23.0 (13.5)* |

| Control | Cage 1 | Cage 2 | Cage 3 | Cage 4 | Mean (SD) |
|---|---|---|---|---|---|

Adult mortality

| | | | | | |
|---|---|---|---|---|---|
| Day 21 | 0 | 1 | 0 | 0 | 0.25 (0.50) |
| Day 42 | 1 | 0 | 2 | 2 | 1.25 (0.96) |
| Day 56 | 2 | 0 | 1 | 0 | 0.75 (0.96) |

Number of eggs

| | | | | | |
|---|---|---|---|---|---|
| Day 21 | 71 | 46 | 51 | 91 | 64.8 (20.6) |
| Day 42 | 19 | 33 | 81 | 56 | 47.3 (27.2) |
| Day 56 | 52 | 69 | 68 | 114 | 75.8 (26.7) |

TABLE 1-continued

Efficacy results

Number of pupae

| | | | | | |
|---|---|---|---|---|---|
| Day 21 | 65 | 41 | 40 | 71 | 54.3 (16.1) |
| Day 42 | 17 | 28 | 71 | 47 | 40.8 (23.7) |
| Day 56 | 48 | 61 | 63 | 88 | 65.0 (16.7) |

Number of emerging adults

| | | | | | |
|---|---|---|---|---|---|
| Day 21 | 55 | 39 | 38 | 66 | 49.5 (13.5) |
| Day 42 | 2 | 22 | 59 | 36 | 29.8 (24.0) |
| Day 56 | 42 | 48 | 48 | 76 | 53.5 (15.3) |

While the invention has been described with reference to details of the illustrated embodiments, these details are not intended to limit the scope of the invention as defined in the appended claims. The embodiment of the invention in which exclusive property or privilege is claimed is defined as follows:

What is claimed is:

1. A synthetic polypeptide comprising an amino acid sequence at least 95% identical to SEQ ID NO: 1 or SEQ ID NO: 2.

2. The synthetic polypeptide of claim 1, comprising the amino acid sequence of SEQ ID NO: 1 or SEQ ID NO: 2.

3. The synthetic polypeptide of claim 1 or claim 2, further comprising a pharmaceutically acceptable carrier.

4. A method of eliciting an immune response against horn flies in a subject, comprising administering to the subject a composition comprising the synthetic polypeptide of claim 1, thereby eliciting an immune response to horn flies.

5. The method of claim 4, wherein the synthetic polypeptide comprises SEQ ID NO: 1 or SEQ ID NO: 2.

6. The method of claim 4, wherein the composition comprising the synthetic polypeptide further comprises a pharmaceutically acceptable carrier.

7. The method of claim 4, wherein the composition comprising the synthetic polypeptide further comprises an adjuvant.

8. The method of claim 4, comprising the additional step of administering to the subject a composition comprising the synthetic polypeptide of claim 1 a second time.

* * * * *